United States Patent [19]

Sulskis

[11] Patent Number: 5,076,301
[45] Date of Patent: Dec. 31, 1991

[54] COMBINATION DENTAL PICK AND STORAGE CASE

[76] Inventor: Andrius Sulskis, 42 W. 718 Jens Jensen La., St. Charles, Ill. 60419

[21] Appl. No.: 632,931

[22] Filed: Dec. 24, 1990

[51] Int. Cl.⁵ .............................................. A61C 15/00
[52] U.S. Cl. ..................................................... 132/321
[58] Field of Search ........................ 132/321, 328, 329

[56] References Cited

U.S. PATENT DOCUMENTS

| 1,527,845 | 2/1925 | Daniel | 132/321 |
| 1,969,874 | 1/1933 | Butterfield | 132/329 |
| 2,931,370 | 1/1958 | Jackson | 132/329 |
| 4,040,433 | 8/1977 | Edison | 132/321 |
| 4,800,905 | 1/1989 | Stuart | 132/328 |

Primary Examiner—John J. Wilson
Assistant Examiner—Cindy A. Cherichetti
Attorney, Agent, or Firm—Hill, Van Santen, Steadman, Simpson

[57] ABSTRACT

A combination dental pick and carrying case is provided by an elongated pick element having a head at one end and a pick portion sized to enter the spaces between the teeth of a user at the other end. The pick element is selectively and temporarily stored in a carrying case and is retained in removable assembly therewith by means of a Morse taper.

3 Claims, 1 Drawing Sheet

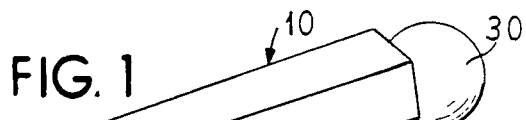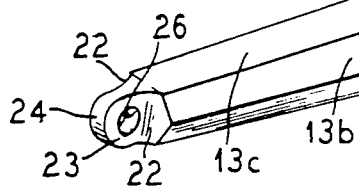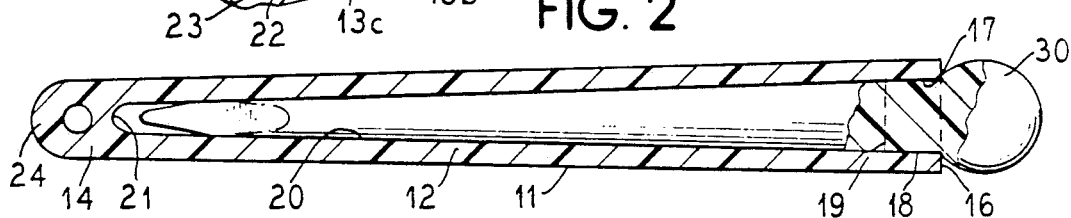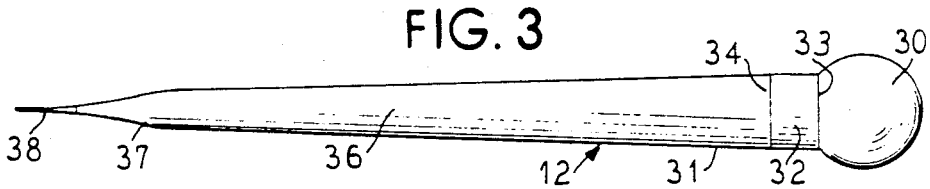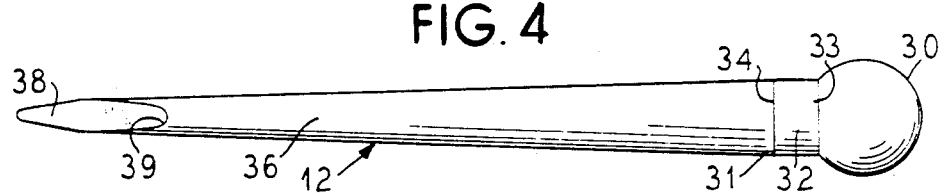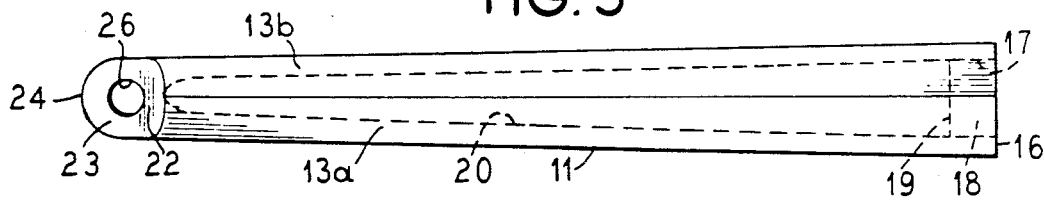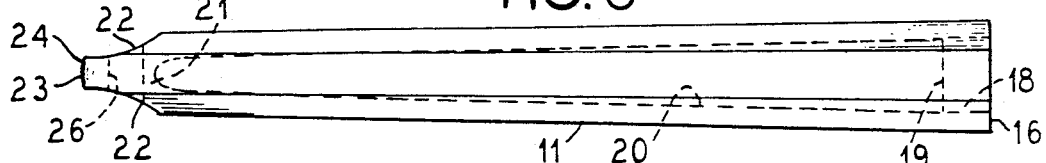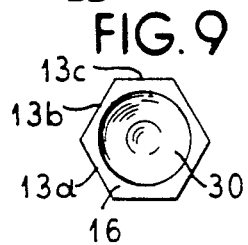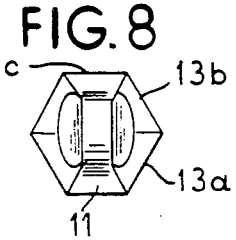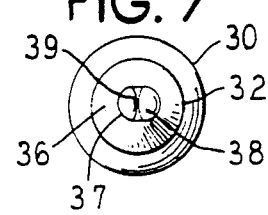

5,076,301

COMBINATION DENTAL PICK AND STORAGE CASE

BACKGROUND OF THE INVENTION

1. Field of the invention

This invention relates generally to a combination dental pick and storage case.

2. Description of the Prior Art

A toothpick is defined in the dictionary as a small pointed piece of wood, plastic, etc., for removing substances, especially food particles, from between the teeth of a user. Articles of that nature have long been provided in different shapes and configurations and on occasion such toothpicks have been provided in the form of metal articles having the appearance of gold or burnished brass with the intent that the user can carry the toothpick and have it available for selective use. Because it is a sharply pointed object, a toothpick is not conveniently retained in the pockets provided by the user's clothing since the pointed end of the device is apt to penetrate the user's clothing and may even cause discomfort or pain to the user when it engages the adjoining body portion or skin.

SUMMARY OF THE INVENTION

In accordance with the principles of the present invention, it is contemplated that there be provided a combination dental pick and storage case wherein an elongated pick element is provided with a head at one end and a pick portion sized to enter the spaces between the teeth of the user at the other end. A correspondingly elongated storage case is provided with an elongated recess formed therein into which the pick element may be selectively inserted. The internal walls of the recess and the external walls of the dental pick are provided with interfitting retaining means, for example, complementary portions together forming a Morse taper by means of which the pick and the storage case may be locked together in removable assembly with one another.

The head portion facilitates ready manipulation of the dental pick by the user and the storage case may have coupling means formed thereon by means of which the device can be fastened to a key chain or to some other readily retrievable object carried on the person of the user.

DESCRIPTION OF THE DRAWINGS

FIG. 1 is a perspective view showing a combination dental pick and storage case provided in accordance with the priciples of the present invention.

FIG. 2 is a view showing the carrying case in cross section and the dental pick inserted therein and shown in elevation.

FIG. 3 is a side elevation of the dental pick and FIG. 4 is a view similar to FIG. 3, but showing the dental pick turned in side elevation by 90°.

FIG. 5 is a side elevational view of the carrying case and FIG. 6 is a view similar to FIG. 5, but showing the carrying case turned through 90°.

FIG. 7 is an end elevational view of the dental pick.

FIG. 8 is an end elevational view of the carrying case and FIG. 9 is an end elevational view showing the dental pick assembled in the carrying case and corresponding to the left-hand side of FIGS. 1 and 2.

DESCRIPTION OF THE PREFERRED EMBODIMENTS

A combination dental pick and carrying case is shown generally at 10 (FIG. 1) and comprises a carrying case 11 suitable for receiving and temporarily storing a dental pick 12.

Although the combination unit 10 may be made of any suitable materials capable of assuming the shapes and configurations contemplated by the present invention, a particularly useful form of the device is provided when the carrying case 11 and the dental pick 12 are made of metal or a suitably rigid plastic.

Referring to FIG. 2, it will noted that the carrying case 11 is essentially an elongated cylinder having walls 12 which are polygonally shaped on the outside, for example, the carrying case 11 may conveniently comprise a hexagon configuration thereby providing external walls 13a, 13b and 13c as shown in FIG. 1, it being understood that a corresponding plurality of walls are formed on the opposite side of the carrying case 11.

Each of the external walls 13a, 13b and 13c form indicia bearing surfaces which may be imprinted or embossed with appropriate indicia, for example, the name of the owner and user and other vital information pertaining to the owner-user. If the device is used as a promotional item, the indicia bearing surfaces formed by the walls 13a, 13b and 13c can carry an appropriate message from the advertiser or the promotion source.

One end of the carrying case 11 is closed as at 14 while the opposite end has a radial wall 16 in which is formed a cylindrical opening 17 forming a mouth or throat of a cylindrical retaining portion 18, which retaining portion terminates at 19.

Extending inwardly from the cylindrical portion 18 the carrying case 11 is formed with an elongated recess which tapers radially inwardly and extends longitudinally, thereby to provide a recess 20 terminating in an end wall 21.

The carrying case 11 is provided with a coupling member 13 which is integrally formed at one end thereof opposite the end on which is located the radial wall 16. Thus, it will be noted that the external walls of the carrying case are curved inwardly as at 22 (FIG. 6) and terminate in a reduced section 23 having a curved end wall 24.

A through aperture 26 extends through the reduced section 23 thereby permitting a ready coupling with either a key chain, or some other retainer member capable of being retrieved when carried on the person of the user.

Referring now to FIGS. 3, 4, 7, and 9, it will be noted that the dental pick shown generally at 12 has a sphere-shaped head 30 forming a finger graspable actuating portion by means of which the dental pick may be readily manipulated, particularly for insertion and removal from the carrying case 11. The radius of curvature of the spherically-shaped head 30 is selected to be sufficiently great so that an elongated shank portion extends away from the head 30 and is smaller in relative size than the head. The portion of the shank shown at 31 immediately adjacent the head 30 is a cylindrical portion 32 extending between axially or longitudinally spaced lines shown at 33 and 34 respectively. Thus, the cylindrical portion 32 essentially matches or is complementary to the corresponding cylindrical portion 18 of the carrying case 11 and when inserted therein, the cylindrical portion 32 of the shank 31 and the cylindrical portion 18 of the carrying case 11 form a Morse taper which will selectively retain the dental pick in assembly with the carrying case.

Extending longitudinally and axially from the cylindrical portion 32, the shank of the dental pick 12 tapers radially inwardly so that the dental pick assumes a general conical configuration shown at 36.

Near the free end of the shank 31, the conical portion 36 is flattened as at 37 to form a sharpened point 38 which is thin enough to conveniently fit between the spaces of the user's teeth. As shown on FIG. 4, the shape of the flattened point is essentially triangular at the free end of the dental pick 12 and at the point of merger with the shank 31 there is formed a curve transition area 39.

In usage, the dental pick is conveniently held by the user via the finger manipulable head 30 and the flattened sharpened point 38 is used to remove food or other substances from between the teeth of the user.

When it is desired to temporarily store the dental pick, it is simply inserted through the opening 17 into the recess 20 of the carrying case 11. The shape of the recess 20 and the configuration of the tapered shank 36 is complementary and the dental pick 12 freely enters into the recess. When the head 30 is near engagement with the radial end wall 16 of the carrying case 11, the cylindrical portion 32 of the dental pick 12 will cooperatively engage with the corresponding cylindrical portion 18 of the carrying case 11 and together will effect a Morse joint connection between the inner and outer elements, thereby retaining the same in selective firm assembly with one another.

Although minor modifications might be suggested by those versed in the art, it should be understood that I wish to embody within the scope of the patent warranted hereon all such modifications as reasonably and properly come within the scope of my contribution to the art.

I claim as my invention:

1. A combination dental pick and carrying case sold as a unit comprising a pick element and a holder element in removable assembly with one another,
   said pick member comprising:
   an elongated member having a ball-shaped head,
   an axially extending cylindrical shaft portion of lesser diameter than said ball-shaped head and projecting longitudinally away from said head.
   an elongated conically-shaped shank tapering axially and radially inwardly relative to said cylindrical shaft portion and extending longitudinally in coaxial alignment with said shaft portion,
   and a tip on the end of said shank comprising a flattened portion which has an ovate transition area at one end and which tapers inwardly to a flat thin configuration sized to enter the spaces between adjacent teeth of a user,
   said holder element comprising:
   an elongated cylinder having first and second ends with an external wall shaped in the configuration of a polygon to form a plurality of indicia bearing surfaces extending between said ends,
   a reduced coupling portion with an caperture on one of the ends of said cylinder through which a key ring or the like may be inserted,
   said cylinder having an axial recess formed therein extending from an opening in the other of said ends into the interior of said cylinder, but terminating short of said one of said ends and shaped to receive said pick element,
   said holder element having a cylindrical retaining portion formed immediately adjacent the said opening and sized and shaped so that together with said shaft portion on the pick element is formed an interfitting Morse taper to retain said pick element in selectively removable assembly with said holder element.

2. A combination dental pick and carrying case as defined in claim 1 wherein said axial recess in said cylinder tapers axially and radially inwardly to complement the shape of the pick element.

3. A combination dental pick and carrying case as defined in claim 1, said dental pick comprising an elongated shaft element made of a rigid material capable of being molded or machined and shaped to provide:
   a spherical ball-shaped head at one end,
   a flattened thin pick area at the opposite end of sufficiently thin dimension to enter the spaces between the teeth of a user, and
   an intermediate shank portion having retainer means formed thereon adapted to engage the adjoining walls of the carrying case.

* * * * *